United States Patent [19]

DeFilippi

[11] 4,343,901
[45] Aug. 10, 1982

[54] MAGNETIC SUPPORT MATRIX FOR ENZYME IMMOBILIZATION

[75] Inventor: Louis J. DeFilippi, Mount Prospect, Ill.

[73] Assignee: UOP Inc., Des Plaines, Ill.

[21] Appl. No.: 199,161

[22] Filed: Oct. 22, 1980

[51] Int. Cl.³ .............................................. C12N 11/14
[52] U.S. Cl. .................................. 435/176; 252/430; 435/177; 435/180
[58] Field of Search .............. 435/174, 176, 177, 180, 435/182; 252/430, 448, 466; 424/1

[56] References Cited

U.S. PATENT DOCUMENTS

| | | | |
|---|---|---|---|
| 2,620,314 | 12/1952 | Hoekstra | 252/448 |
| 4,102,746 | 7/1978 | Goldberg | 435/176 X |
| 4,141,857 | 2/1979 | Levy et al. | 252/430 |
| 4,152,210 | 5/1979 | Robinson et al. | 435/176 |
| 4,177,253 | 12/1979 | Davies et al. | 424/1 |
| 4,199,614 | 4/1980 | Ziolo | 430/111 |
| 4,289,655 | 9/1981 | Bailey | 252/466 B |

OTHER PUBLICATIONS

Halling et al., Magnetic Supports for Immobilized Enzymes and Bioaffinity Adsorbents, Enzyme Microb. Technol., vol. 2, 1980, (pp. 2–11).

Primary Examiner—David M. Naff
Attorney, Agent, or Firm—James R. Hoatson, Jr.; Eugene I. Snyder; William H. Page, II

[57] ABSTRACT

A magnetic support matrix for enzyme immobilization is prepared which comprises a porous, refractory inorganic oxide containing ferromagnetic particles dispersed throughout its interior and a polyamine cross-linked with an excess of a bifunctional reagent impregnated therein so as to furnish pendant functional groups. Such a magnetic support matrix does not otherwise substantially decrease loading of subsequently immobilized enzyme, nor in any other way substantially alter the properties of the immobilized enzyme system when compared to that prepared on a non-magnetic support.

17 Claims, No Drawings

MAGNETIC SUPPORT MATRIX FOR ENZYME IMMOBILIZATION

BACKGROUND OF THE INVENTION

Enzyme-catalyzed reactions have the advantages of proceeding with great chemical specificity under relatively mild conditions, and often accomplish what man finds difficult, if not impossible, to duplicate in the laboratory. For such reasons there is increasing emphasis on the use of enzymatic processes on a commercial scale. One example, of many which could be cited, is the conversion of glucose to fructose using glucose isomerase.

Enzymes often are water soluble, and if they are merely used in aqueous solutions recovery of enzymes for reuse is difficult and expensive. Using the enzyme only once affords a process which is relatively expensive. Consequently, many techniques have been developed for immobilizing the enzyme in such a way that substantial enzymatic activity is displayed while the enzyme itself remains rigidly attached to some water-insoluble support, thereby permitting reuse of the enzyme over substantial periods of time and for substantial amounts of feedstock. One illustration of a method for immobilizing an enzyme is found in U.S. Pat. No. 4,141,857, where a polyamine is absorbed on a metal oxide such as alumina, treated with an excess of a bifunctional reagent, such as glutaraldehyde, so as to cross-link the amine, and then contacting the mass with enzyme to form covalent bonds between the pendant aldehyde groups and an amino group on the enzyme. The support matrix prepared according to the aforementioned invention has great utility in immobilizing reactive chemical entities, enzymes being but one class of such reactive chemical entities.

An immobilized enzyme system is the material which results from immobilization of an enzyme onto a support matrix. Magnetic support matrices and immobilized enzyme systems offer several advantages when compared to non-magnetic systems. For example, separation of such materials from other non-magnetic solids by use of a magnetic field can permit separations otherwise difficult or impossible to perform. Such a situation is represented by the case where two enzymes, with different deactivation times, are used concurrently on a substrate, with one immobilized enzyme system magnetic and the other non-magnetic. In this case, after one enzyme is exhausted, the other may be readily recovered and reused by magnetic separation of the two immobilized enzyme systems, which will be recognized as offering great benefits in economy. Another advantage of such magnetic materials is their use in a magnetically stabilized fluid bed, thereby presenting further options in continuous reactor systems.

U.S. Pat. No. 4,152,210 describes a support matrix comprised of particulates of ferromagnetic materials. Enzymes are bound thereto by reagents which react with a film of metal oxide on the surface of the particulates, or to polymeric material attached to the support. A serious disadvantage of such a support matrix is its high density. This disadvantage is overcome in U.S. Pat. No. 4,177,253 which describes a ferromagnetic composite comprising a low density core whose surface is coated with magnetic materials. Because more than 50% of the surface must be so coated, the latter support matrix presents the disadvantage of reducing the number of sites available for subsequent enzyme bonding, thus presenting substantial limitations on the amount of enzyme which can be immobilized. Additionally, because a surface coating of ferromagnetic material necessitates a method of preparation which is reasonably elaborate, complex, and demanding, such supports can be expected to be reasonably expensive and commercially unfeasible. Magnetic supports for immobilized enzymes and bioaffinity adsorbents has been reviewed by Halling and Dunnill, *Enzyme Microb. Technol.,* 2, 2–10 (1980).

It is highly desirable to have a magnetic support matrix whose only difference from a conventional one is its magnetic properties, and which can be readily prepared by simple procedures. In part this dictates a magnetic support whose ferromagnetic materials are not bound as a surface coating and which may be prepared by a variation in the basic method of preparation.

SUMMARY OF THE INVENTION

An object of this invention is to provide a magnetic, porous support matrix. An embodiment comprises a porous refractory inorganic oxide through the interior of which are dispersed particles of ferromagnetic materials, said oxide being impregnated with a polyamine cross-linked with an excess of a bifunctional reagent so as to furnish pendant functional groups. In a more specific embodiment the particles are at least 0.05 microns in size and selected from the group consisting of iron, cobalt, and nickel. In a still more specific embodiment, the polyamine is polyethyleneimine and the bifunctional reagent is glutaraldehyde.

DESCRIPTION OF THE INVENTION

The support matrices of U.S. Pat. No. 4,141,857 are broadly effective and have enjoyed wide success for diverse enzymes. This application describes support matrices incorporating advantages accruing to a magnetic support matrix while utilizing the benefits of the support matrix described in the cited patent. Briefly described, the support matrix of this invention comprises a porous, refractory inorganic oxide through the interior of which are dispersed particles of ferromagnetic materials, said oxide being impregnated with a polyamine cross-linked with an excess of a bifunctional reagent so as to furnish pendant functional groups.

Among the porous refractory inorganic oxides of this invention are included alumina, thoria, magnesia, silica, and combinations thereof, with alumina being preferred. Such oxides may be in the form of granules or powder with a size as small as about 100 mesh, as spheres, as pellets, as extrudate, and so forth.

A point of novelty of this invention is that there is dispersed throughout the interior of such oxides particles of magnetic or ferromagnetic materials. The dispersion of ferromagnetic particles occurs more or less uniformly throughout the body of the oxide. Because of such uniform dispersion, some ferromagnetic particles will be on the surface of the oxide. However, it is to be recognized and emphasized that the presence of some ferromagnetic materials on the surface is incidental to this invention and does not form any part of it. It must also be recognized that only a relatively small fraction of the ferromagnetic particles will be on the surface, this fraction being less than, and generally substantially less than, about 10% of the total.

The particle size of the ferromagnetic materials generally will be greater than about 0.05 microns. A lower limit is dictated by the necessity of preventing a substantial portion of the ferromagnetic material from being oxidized to a non-ferromagnetic state. Where the product of the ferromagnetic material is itself ferromagnetic, this lower limit in particle size may not be applicable. An upper limit is dictated by the desirability that the diameter of the formed oxide particles be at least about ten times the diameter of ferromagnetic materials dispersed through its interior. Thus, particle size may be as great as about 0.5 mm, with the range from about 0.1 micron to about 0.1 mm being preferred, and sizes from about 0.5 micron to about 50 microns being still more preferred.

The ferromagnetic materials which may be used in this invention include all appropriate materials having ferromagnetic properties. Examples of such ferromagnetic materials include nickel, various ferromagnetic steels such as carbon steel, chromium steel, tungsten steel, cold rolled steel, cobalt steel, for example, ferromagnetic alloys exemplified by Ferroxdur, Oerstit, Permalloy, Hipernik, Ferroxcube, Sinimax, Alnico, Hycomax, Remalloy, Hyflux, and other alloys as listed in the CRC Handbook, 50th Ed., E-124 to E-129, and compounds, such as magnetite, of the above metals which are themselves ferromagnetic. Such ferromagnetic materials are present from about 1 to about 40 wt.% based on the inorganic oxide.

The inorganic oxide having ferromagnetic particles dispersed through its interior is impregnated with a polyamine subsequently cross-linked with an excess of a bifunctional reagent so as to furnish pendant functional groups. Among the polyamines which can be successfully used are included polyethyleneimine, tetraethylenepentamine, ethylenediamine, diethylenetriamine, triethylenetetramine, pentaethylenehexamine, hexamethylenediamine, and phenylenediamine. Among these materials polyethyleneimine is especially preferred.

The bifunctional reagent serves simultaneously to crosslink the polyamine, thereby affording a firmly attached layer, and to furnish pendant functional groups which can subsequently react with an enzyme so as to bind it to the support matrix. Among the bifunctional reagents which may be used are included glutaraldehyde, succindialdehyde, terephthaldehyde, and toluenediisocyanate, with glutaraldehyde being somewhat preferred.

Immobilized enzyme systems result from coupling, or binding, an enzyme to the support matrix. Therefore, such immobilized enzyme systems comprise the support matrix with the enzyme bound thereto. Examples of enzymes which may be used, intended to be merely representative of the group, include glucose isomerase, glucoamylase, lactase, cellulase, glucose oxidase, peroxidase, ribonuclease, urease, histidinase, trypsin, papain, hexokinase, chymotrypsin, acylase, invertase, ficin, lysozyme, protease, pepsin, rennin, xylanase, beta amylase, gamma amylase, asparaginase, cholesterol oxidase, alcohol dehydrogenase, amino acid oxidase, collagenase, arginase, catalase, and deoxyribonuclease.

The support matrix of this invention may be made by first generating the porous refractory inorganic oxide in the presence of a fine dispersion of ferromagnetic material. For example, an alumina sol may be mixed with a suspension of ferromagnetic material of the desired size and in a ratio so as to give the desired percentage of ferromagnetic material. The sol is then caused to gel quickly so that the solid oxide is formed around the dispersed particles of ferromagnetic materials, resulting in the latter becoming more or less uniformly dispersed throughout the oxide. The sol is then calcined, for example, at about 650° C. for about two hours, under conditions where the ferromagnetic material is not oxidized to a nonferromagnetic state. For example, where particles of nickel greater than about two microns are used, calcination may be performed in air. However, when magnetite of the same size is used, calcination must be performed in an inert or non-oxidizing atmosphere, such as nitrogen, hydrogen, argon, and so forth.

After preparing the oxide with ferromagnetic particles dispersed through its interior, the preparation of the support matrix is completed as described in U.S. Pat. No. 4,141,857.

The examples cited below are merely illustrative of this invention and are not to be construed as limitations thereof.

EXAMPLE 1

The porous, refractory inorganic oxide containing dispersed particles of ferromagnetic materials were prepared by the oil dropping process according to U.S. Pat. No. 2,620,314. An alumina sol was prepared by reacting aluminum pellets of 99.9% purity with reagent hydrochloric acid and deionized water to afford material with an aluminum to chlorine ratio of 1.35 containing 12.62% by weight aluminum. There was mixed 500 ml of sol, 500 ml of 28 wt.% hexamethylenetetramine solution and 16 g of magnetite ($Fe_3O_4$) having an average particle size of 0.7 microns. Droplets of 1/16" diameter were formed and passed through an 8' column of oil at 95° C. The spheres were collected in a stainless steel beaker, covered with hot oil and placed in an oven at 100° C. for 19 hours. These then were transferred to a wash tower and 5 gallons of 1% aqueous ammonia at 95° were passed over the spheres during 6 hours. The spheres were then washed with 5 gallons of 0.01% aqueous ammonia over 7 hours and dried at 120° C. for 4 hours.

This material was calcined under nitrogen at 650° C. for 1 hour, the resulting material being magnetic. However, when the material was calcined in air at 650°–660° C. for about 1.5 hours, virtually none of the material was magnetic.

EXAMPLE 2

Alumina containing nickel was prepared by a procedure similar to that above. There was employed 600 ml of a sol (aluminum to chlorine ratio 1.62 at 12% by weight aluminum), 600 ml 28% by eight hexamethylenetetramine solution, and 18 grams of nickel powder, average particle size 1.4 microns. Calcination was performed in a nitrogen-hydrogen atmosphere (about 90% nitrogen) at 600° C. for 1 hour and 650° C. for ¼ hour at a flow rate of 2 liters per minute. The material so prepared was magnetic. Similar calcinations under nitrogen and in air also afforded magnetic material. Even when calcination was performed under air at 650° C. for 3.5 hours the sample remained magnetic.

EXAMPLE 3

A sample of nickel in alumina as prepared in Example 2 and calcined under 90% nitrogen-hydrogen was ground and seived to a 25/35 mesh size, a 1 gram sample was treated with 10 ml of 1.5% polyethyleneimine for 1 hour under vacuum. The resulting polyamine impregnated material was dried on a Buchner funnel, then left to further dry overnight on filter paper. A 0.5 gram sample of dried solid was treated with 5 ml of 1% glutaraldehyde with occasional mixing. Liquid was decanted and solid was exhaustively washed with deionized water until a negative Fuchsin aldehyde test was observed for the washings. The resulting solid was shaken with about 10 ml of a solution containing about 1,700 international units of glucose isomerase for about 18 hours. Excess enzyme solution was decanted, and the immobilized enzyme system was washed well with deionized water to remove adhering but unbound enzyme. The material so prepared was analyzed in a reactor flow system using 45% fructose as feedstock containing 5 mM magnesium sulfate at pH 8.0. Analysis of the effluent by high pressure liquid chromatography for glucose content showed an activity of 961 international units per gram. Immobilized glucose isomerase prepared on 25/35 mesh alumina, similar in all regards except for lack of nickel incorporation, showed activities of about 1,000 units per gram. Therefore, the immobilized glucose isomerize showed comparable activities on the magnetic and non-magnetic supports.

What is claimed is:

1. A magnetic support matrix comprising a porous, refractory inorganic oxide selected from the group consisting of alumina, thoria, magnesia and combinations thereof, through the interior of which are dispersed particles, from about 0.05 micron to about 0.5 mm in size, of ferromagnetic materials in an amount from about 1 to about 40 percent by weight with less than about 10 percent of said particles on the surface of the oxide, said oxide being impregnated with a polyamine cross-linked with an excess of a bifunctional reagent so as to furnish pendant functional groups.

2. The support matrix of claim 1 wherein the oxide is alumina.

3. The support matrix of claim 1 where said ferromagnetic materials are selected from the group consisting of iron, cobalt, nickel, magnetite and their ferromagnetic alloys and compounds.

4. The support matrix of claim 1 wherein the size of the particles of ferromagnetic materials are from about 0.5 to about 50 microns.

5. The support matrix of claim 1 wherein the polyamine is selected from the group consisting of polyethyleneimine, tetraethylenepentamine, ethylenediamine, diethylenetriamine, triethylenetetramine, pentaethylenehexamine, hexamethylenediamine, and phenylenediamine.

6. The support matrix of claim 5 wherein the polyamine is polyethyleneimine.

7. The support matrix of claim 1 wherein the bifunctional reagent is selected from the group consisting of glutaraldehyde, succindialdehyde, terephthaldehyde, and toluenediisocyanate.

8. The support matrix of claim 7 wherein the bifunctional reagent is glutaraldehyde.

9. A magnetic immobilized enzyme system comprising a porous, refractory inorganic oxide selected from the group consisting of alumina, thoria, magnesia and combinations thereof through the interior of which are dispersed particles, from about 0.05 micron to about 0.5 mm in size, of ferromagnetic materials in an amount from about 1 to about 40 percent by weight, with less than about 10 percent of said particles on the surface of the oxide, said oxide being impregnated with a polyamine cross-linked with an excess of a bifunctional reagent so as to furnish pendant functional groups, with an enzyme bound thereto.

10. The immobilized enzyme system of claim 9 where the oxide is alumina.

11. The immobilized enzyme system of claim 9 where said ferromagnetic materials are selected from the group consisting of iron, cobalt, nickel, magnetite and their ferromagnetic alloys and compounds.

12. The immobilized enzyme system of claim 9 wherein the size of the particles of ferromagnetic materials are from about 0.5 to about 50 microns.

13. The immobilized enzyme system of claim 9 wherein the polyamine is selected from the group consisting of polyethyleneimine, tetraethylenepentamine, ethylenediamine, diethylenetriamine, triethylenetetramine, pentaethylenehexamine, hexamethylenediamine, and phenylenediamine.

14. The immobilized enzyme system of claim 13 wherein the polyamine is polyethyleneimine.

15. The immobilized enzyme system of claim 9 wherein the bifunctional reagent is selected from the group consisting of glutaraldehyde, succindialdehyde, terephthaldehyde, and toluenediisocyanate.

16. The immobilized enzyme system of claim 15 wherein the bifunctional reagent is glutaraldehyde.

17. The immobilized enzyme system of claim 9 where the enzyme is selected from the group consisting of glucose isomerase, glucoamylase, lactase, cellulase, glucose oxidase, peroxidase, ribonuclease, urease, histidinase, trypsin, papain, hexokinase, chymotrypsin, acylase, invertase, ficin, lysozyme, protease, pepsin, rennin, xylanase, beta amylase, gamma amylase, asparaginase, cholesterol oxidase, alcohol dehydrogenase, amino acid oxidase, collagenase, arginase, catalase, and deoxyribonuclease.

* * * * *